United States Patent
Greil et al.

(12) United States Patent
(10) Patent No.: US 6,949,641 B2
(45) Date of Patent: Sep. 27, 2005

(54) CRYSTALLINE β-LACTAM INTERMEDIATE

(75) Inventors: Julia Greil, Kramsach (AT); Johannes Ludescher, Breitenbach (AT); Klaus Totschnig, Kundel (AT); Siegfried Wolf, Brixlegg (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/001,544

(22) Filed: Oct. 31, 2001

(65) Prior Publication Data

US 2002/0065262 A1 May 30, 2002

Related U.S. Application Data

(63) Continuation of application No. PCT/EP00/03941, filed on May 3, 2000.

(30) Foreign Application Priority Data

May 5, 1999 (AT) ................................................ 799/99

(51) Int. Cl.$^7$ ............................................. C07D 501/34
(52) U.S. Cl. ...................................... 540/220; 540/228
(58) Field of Search .................................. 540/222, 228

(56) References Cited

U.S. PATENT DOCUMENTS

| 4,486,425 A | 12/1984 | Nakao et al. |
| 5,461,043 A | 10/1995 | Fischer et al. |
| 6,489,470 B1 * | 12/2002 | Greil et al. ................. 540/220 |

FOREIGN PATENT DOCUMENTS

| JP | 60-004189 | | 1/1985 | |
| JP | 3-031286 | | 2/1991 | |
| JP | 03031286 A | * | 2/1991 | ......... C07D/501/04 |
| JP | 60-67483 | * | 3/1994 | |
| WO | WO 99 35149 A | | 7/1999 | |
| WO | WO 200109143 A1 | * | 2/2001 | ........... C07D/00/00 |
| WO | WO 200134611 A1 | * | 5/2001 | ......... C07D/501/36 |

OTHER PUBLICATIONS

Patent Abstracts of Japan, vol. 009, No. 112 (JP 60 004189 A) (Jan. 10, 1985).
Patent Abstracts of Japan, vol. 015, No. 154 ( JP 03 031286 A (Feb. 12, 1991) Derwent Abstract 1991–084514 [12]).

* cited by examiner

*Primary Examiner*—Mark L. Berch
(74) *Attorney, Agent, or Firm*—John D. Thallemer

(57) ABSTRACT

The novel intermediate compound crystalline 7-[2-(2-fomylaminothiazol-4-yl)-2 -(Z)-(methoxyimino) acetamido]-3-methoxymethyl-3-cephem-4-carboxylic acid-1 -(isopropoxy/crystallization of cefpodoxime proxetil. The crystallization process comprises dissolving or suspending the intermediate in the presence of a nitrile or a ketone or mixtures thereof; at a ratio of 1 gm of the intermediate to 2–15 ml nitrile; or at a ratio of 1 gm of the intermediate to 3–15 ml ketone; in the presence of 5–80 ml water; and thereafter isolating the intermediate in crystalline form and converting the intermediate by splitting off the formyl group from the amino group attached to the thiazolyl group, to obtain the desired product cefpodoxime proxetil, in the form of a diastereoisomeric mixture in a ratio of B/(A+B) of 0.5 to 0.6.

10 Claims, No Drawings

CRYSTALLINE β-LACTAM INTERMEDIATE

This is a continuation of International Application No. PCT/EP 00/03941, filed May 3, 2000.

The present invention relates to β-lactams, particularly to cefpodoxime proxetil, of formula

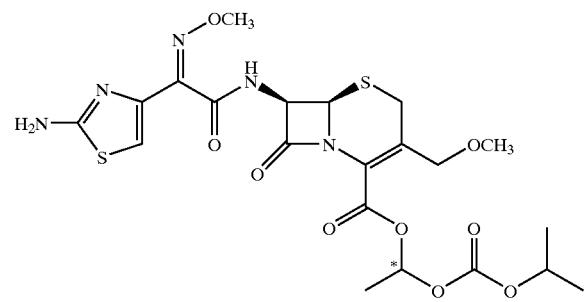

II e.g. described in The Merck Index, Twelfth Edition, Item 1991; more particularly to a process for the adjustment, e.g. change, of the diastereoisomeric ratio of the two existing diastereoisomers being with respect to the carbon atom attached to the oxygen of the ester group in the carboxyl ester group in position 4 of the ring system (marked with a star (*) in formula II). A diastereoisomeric ratio B/(A+B) of cefpodoxime proxetil currently on the market may be around 0.53. B is the more apolar of the two diastereoisomers. Because of different bioavailability of these individual diastereoisomers a commercial form for oral administration of cefpodoxime proxetil has to be within a defined ratio B/(A+B). A diastereoisomeric ratio B/(A+B) of 0.5 to 0.6 has been found to be bioequivalent with a commercial form. Determination of the diasterisomeric content of the diastereoisomers A and B in cefpodoxime proxetil may be carried out by HPLC, e.g. according to a method as described in Pharmacopeial Forum, Vol. 23, No. 4, p. 4388 ff (1997), the content of which is incorporated herein by reference, e.g. from which a diastereoisomeric ratio B/(A+B) and A/(A+B) may be calculated.

One process in the production of cefpodoxime proxetil may be carried out via acylation of 7-amino-3-methoxymethyl-3-cephem-4-carboxylic acid-1-(isopropoxycarbonyloxy)ethyl-ester of formula

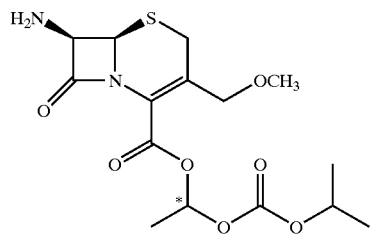

III with activated Z-2-(methoxyimino)-2-(2-formylaminothiazol-4-yl)-acetic acid to obtain 7-[2-(2-formylaminothiazol-4-yl)-2-(Z)-(methoxyimino) acetamido]-3-methoxymethyl-3-cephem-4-carboxylic acid 1-(isopropoxycarbonyloxy)ethyl ester (N-formyl cefpodoxime proxetil) of formula

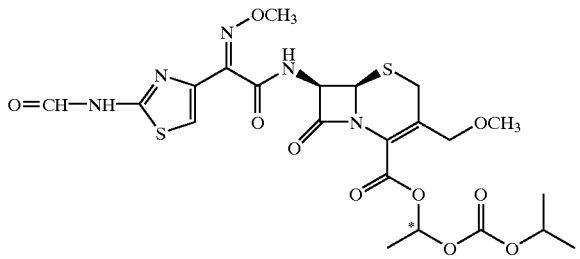

I

It was found that a mixture of diastereoisomers of a compound of formula I may be obtained in a diastereoisomeric ratio B/(A+B) of 0.40 to below 0.50. The reaction for splitting off the formyl group in a compound of formula I obtained to obtain cefpodoxime proxetil may have no significant influence on the diastereoisomeric ratio B/(A+B) and consequently B/(A+B) in cefpodoxime proxetil obtained from a process as described above may be outside of 0.5 to 0.6.

Surprisingly a simple process has now be found wherein cefpodoxime proxetil may be obtained in high purity; e.g. in a diastereoisomeric ratio which is 0.4 to 0.7, e.g. 0.5 to 0.6.

A compound of formula I may be produced, e.g. in conventional manner and e.g. as follows:

The carboxylic acid group in position 4 of the ring system of 7-amino-3-methoxymethyl-3-cephem-4-carboxylic acid (AMCA), e.g. of formula

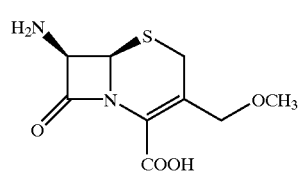

IV which is a known compound and obtainable, e.g. according to a method as conventional, may be esterified to obtain a compound of formula III. This may be effected according to a method as conventional, e.g. by reacting AMCA with a compound of formula

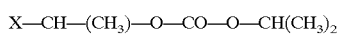

X—CH—(CH₃)—O—CO—O—CH(CH₃)₂    V wherein X denotes a leaving group, e.g. a conventional leaving group, such as a halogenide, e.g. an iodide; e.g. in the presence of a solvent (system). Esterification may be effected e.g. in conventional solvent (system), e.g. organic solvent, such as ketones, e.g. acetone; nitriles, e.g. acetonitrile; acetamides, e.g. dimethylacetamide; and halogenated hydrocarbons, e.g. dichloromethane; and e.g. in the presence of a base; e.g. an amidine, such as 1,5-diazabicyclo(4,3,0) non-5-ene (DBN) or 1,8-diazabicyclo(5,4,0)undec-7-ene (DBU); or a guanidine, e.g. a linear guanidine, such as tetramethylguanidine, pentamethylguanidine, tetraethylguanidine, tetramethylethylguanidine and tetramethylbenzylguanidine or a cyclic or bicyclic guanidine, e.g. 1,5,7-triazabicyclo-(4,4,0)-dec-5-ene, and 7-methyl, 7-ethyl, 7-benzyl and 7-phenyl derivatives thereof. A compound of formula III obtained may be isolated, if desired, e.g. according to a method as conventional.

The amine group in position 7 of the ring structure of a compound of formula III, e.g. obtained as described above, e.g. with or without isolation from a corresponding reaction mixture, preferably without isolation, may be acylated e.g. according to a method as conventional. This may be effected e.g. by reaction of a compound of formula III obtained in the esterification reaction, with activated Z-(2-formylaminothiazol-4-yl)-methoxyimino acetic acid, e.g. including an ester or an acid halogenide, such as Z-(2-formylaminothiazol-4-yl)-methoxyimino-acetic acid chloride, e.g. in the form of a salt, e.g. a hydrochloride, including activated Z-(2-formamidothiazol-4-yl)-methoxyimino acetic acid obtainable by a Vilsmeier reaction. Vilsmeier activated Z-(2-formamidothiazol-4-yl)-methoxyimino acetic acid may be produced e.g. in conventional manner, e.g. in situ in the reaction mixture e.g. by treating Z-(2-formamidothiazol-4-yl)-methoxyimino acetic acid with phosphoroxyhalogenide, e.g. chloride, e.g. under Vilsmeier reaction conditions.

Acylation may be carried out in organic solvent (system), including e.g. carboxylic acid esters, e.g. acetates, such as ethyl acetate; halogenated hydrocarbons, e.g. aliphatic, such as dichloromethane, e.g. in dichloromethane; in the presence of a nitrite or a ketone; e.g. in the presence of an amide, e.g. N,N-dimethylformamide (DMF); e.g. in the presence of pH adjustment. pH Adjustment may be effected e.g. by addition of a base, such as an inorganic base, e.g. a carbonate or bicarbonate, e.g. sodium and potassium, or e.g. of an, e.g. weakly, basic anionic exchange resin, to obtain a pH of ca. 2.5 to 8.0. Surprisingly pH adjustment may alternatively also be avoided. A compound of formula I may be obtained in the reaction mixture. According to the present invention a compound of formula I may be obtained in crystalline form.

A compound of formula I in crystalline form may be produced as follows:

N-formyl cefpodoxime proxetil may be suspended or dissolved in a nitrite, or in a ketone; e.g. including mixtures thereof; and may crystallise, e.g. and water may be added to the mixture.

A nitrile, e.g. a $(C_{2-5})$nitrile, includes for example acetonitrile, propionitrile or butyronitrile, preferably acetonitrile. A ketone, e.g. a $(C_{2-4})$ketone, includes for example acetone or methyl ethyl ketone, preferably acetone.

The temperature during crystallisation is not critical. A compound of formula I may crystallise at, below, or higher than room temperature, e.g. at room temperature; in an ice-bath, or up to 70° C. Temperatures of 20 to 40° C. are preferred.

Crystallisation of a compound of formula I from organic solvent comprising a nitrite or a ketone may result in a mixture of diastereoisomers of a compound of formula I in a diastereoisomeric ratio B/(A+B) of 0.4 to 0.7.

We have found surprisingly that water may have an influence in respect with a desired diastereoisomeric ratio of N-formyl cefpodoxime diastereoisomers and that a diastereoisomeric ratio of 0.5 to 0.6 may be adjusted by addition of appropriate amounts of water to a mixture containing a compound of formula I and a nitrile or a ketone.

Alternatively, N-formyl cefpodoxime proxetil may be suspended or dissolved, preferably dissolved, in organic amide or urea, preferably in organic amide, for example DMF, or in organic amide in combination with a ketone, for example acetone; a nitrile, for example acetonitrile; an ester, for example ethyl acetate; or a halogenated hydrocarbon, for example dichloromethane, e.g. dichloromethane in combination with a nitrile or a ketone. If not already present a nitrile or a ketone, e.g. and water, is added to the mixture obtained. A compound of formula I may crystallise and may be obtained in crystalline form, e.g. a mixture of diastereoisomers of a compound of formula I in a diastereoisomeric ratio B/((A+B) of 0.4 to 0.7, such as 0.5 to 0.6 may be obtained.

The ratio of water/organic solvent is critical, not only for crystallisation, but for a desired diastereoisomeric ratio and for a high purification effect of a compound of formula I. Higher amount of organic solvent may result in a higher diastereoisomeric ratio B/(A+B). E.g. from pure acetonitrile as a solvent a compound of formula I may be obtained in a diastereoisomeric ratio B/(A+B) of 0.63.

If too much water is present, the purification effect in the crystallisation step may be insufficient. An appropriate amount of water may easily be found out, e.g. by determining purity and the diastereoisomeric ratio B/(A+B) for different amounts of water present. Preferred solvent ratios include e.g. 2 to 15 ml, preferably 3 to 10 ml of a nitrile, preferably acetonitrile, and 5 to 80 ml, preferably 10 to 50 ml of water, based on 1 g of a compound of formula I. The solvent ratio may also depend whether and in which amount an organic amide e.g. DMF is present. E.g. DMF may be present in the solvent system, e.g. 1 to 20 ml, preferably 2 to 15 ml; DMF per g of a compound of formula I.

If a compound of formula I is crystallised from a ketone, e.g. acetone and water, preferred amounts of acetone and water include 3 to 15 ml, preferably 3 to 10 ml of a ketone, e.g. acetone; and 10 to 40 ml, preferably 15 to 30 ml of water; per g of a compound of formula I.

N-formyl cefpodoxime proxetil may also be produced directly from a reaction mixture wherein N-formyl cefpodoxime is obtained, e.g. as follows:

To a mixture containing a compound of formula I, e.g. obtained in a corresponding reaction an organic amide, e.g. DMF or urea is added, e.g. if not already present; and solvent is removed, e.g. by distillation, evaporation. The residue obtained is mixed with a nitrile or a ketone; e.g. and water. Alternatively, if acylation is carried out in dichloromethane, a nitrile or a ketone may be added after removal of the solvent; e.g. and water may be added to the residual mixture obtained. N-Formyl cefpodoxime proxetil may crystallise and may be isolated from the reaction mixture, e.g. according to a method as conventional. Crystalline N-formyl cefpodoxime proxetil in crystalline form is new.

In one aspect the present invention provides a compound of formula I in crystalline form.

Production of a compound of formula I in crystalline form may have a high purification effect, e.g. in (part of) a production sequence from AMCA to N-formyl cefpodoxime.

We have surprisingly additionally found, that N-formyl cefpodoxime produced according to the present invention may crystallise in a diastereoisomeric ratio B/(A+B) of 0.5 to 0.6.

In another aspect the present invention provides a process for the production of a compound of formula I in crystalline form, e.g. a mixture of diastereoisomers of a compound of formula I, comprising crystallizing a compound of formula I in organic solvent comprising a nitrile, e.g. a $(C_{2-4})$nitrile; or a ketone, e.g. a $(C_{3-5})$ketone; e.g. in the presence of water, e.g. wherein the diastereoisomeric ratio B/(A+B), wherein B is the more apolar of the two diastereoisomers, is 0.5 to 0.6, the diastereoisomers being with respect with the carbon atom marked with a star in formula I.

In still another aspect the present invention provides the use of crystalline N-formyl cefpodoxime proxetil in the purification of cefpodoxime proxetil, e.g. in the form of a mixture of diastereoisomers of a compound of formula I, wherein the diastereoisomeric ratio B/(A+B), wherein B is the more apolar of the two diastereoisomers, is 0.5 to 0.6, the diastereoisomers being with respect with the carbon atom marked with a star in formula I.

In another aspect the present invention provides a process for the adjustment, e.g. change, of the diastereoisomeric ratio B/(A+B) wherein B is the more apolar of the two diastereoisomers; of a mixture of diastereoisomers of cefpodoxime proxetil, e.g. adjusting a diastereoisomeric ratio B/(A+B) to 0.5 to 0.6; the diastereoisomers being with respect with the carbon atom marked with a star in formula I, comprising crystallizing a compound of formula I from a mixture comprising water and either a nitrile, e.g. a $(C_{2-5})$ nitrile, or a ketone, e.g. a $(C_{3-5})$ketone; e.g. including mixtures thereof; and converting the crystalline compound of formula I obtained into cefpodoxime proxetil.

In a further aspect the present invention provides a process for the purification of cefpodoxime proxetil, comprising producing a compound of formula I as defined in claim 1 and crystallizing in the presence of a nitrile or a ketone and converting a crystalline compound of formula I into cefpodoxime proxetil.

In still another aspect the present invention provides a process for the production of a mixture of diastereoisomers of cefpodoxime proxetil of formula II in a diastereoisomeric ratio B/(A+B), wherein B is the more apolar of the two diastereoisomers, of 0.5 to 0.6, the diastereisomers being with respect with the carbon atom marked with a star in formula II, comprising producing a mixture of diastereoisomers of a compound of formula I by acylating a compound of formula III with activated Z-(2-formamidothiazol-4-yl)-methoxyimino acetic acid, removing solvent from the reaction mixture obtained, crystallizing a compound of formula I in the residue obtained in the presence of a nitrile or a ketone, e.g. in the presence of water; isolating a compound of formula I in crystalline form and converting a compound of formula I by splitting off the formyl group from the amino group attached to the thiazolyl group, to obtain a compound of formula I, in the form of a diastereoisomeric mixture in a ratio of B/(A+B) of 0.5 to 0.6, e.g. wherein a compound of formula III is produced by esterifying 7-amino-3-methoxymethyl-3-cephem-4-carboxylic acid with a compound of formula V wherein X denotes a leaving group.

Advantages of a process according to the present invention includes e.g.:

Crystallisation of N-formyl cefpodoxime proxetil which may surprisingly carried out according to a process according to the present invention may have a strong purification effect in e.g. part of the reaction sequence of producing cefpodoxime proxetil e.g. starting from AMCA, or AMCA-ester.

A process according to the process of the present invention may be used on technical scale.

A desired diastereoisomeric ratio B/(A+B) may be adjusted in the production of cefpodoxime proxetil, e.g. of 4 to 7 such as of 5 to 6.

In still another aspect the present invention provides a crystalline 7-[2-(2-formylaminothiazol-4-yl)-2-(Z)-(methoxyimino)acetamido]-3-methoxymethyl-3-cephem-4-carboxylic acid-1-(isopropoxycarbonyloxy)ethyl ester of formula I as a diastereoisomeric mixture of formula I (*signifies the asymmetric centre) and a process for the production of the diastereoisomeric mixture of formula I, whereby a compound of formula III is acylated with a reactive derivative of (2-N-formylaminothiazol-4-yl)-2-(Z)-(methoxyimino)-acetic acid and the compound of formula I is crystallised in water and a $(C_{1-4})$nitrile or water and a $(C_{3-5})$ketone, e.g. whereby the compound of formula III is produced by the esterification of 7-amino-3-methoxymethyl-3-cephem-4-carboxylic acid of formula IV with a compound of formula V wherein X signifies a leaving group, in the presence of a base.

In the following examples all temperatures are given in degrees celsius.

The following abbreviations are used:

DMF: N,N-dimethylformamide
AMCA: 7-amino-3-methoxymethyl-3-cephem-4-carboxylic acid
DBU: 1,8-diazabicyclo(5,4,0)undec-7-ene
AMCA-ester: 7-amino-3-methoxymethyl-3-cephem-4-carboxylic acid-1-(isopropoxycarbonyloxy)ethyl ester
N-Formyl cefpodoxime proxetil: 7-[2-(2-formylaminothiazol-4-yl)-2-(Z)-(methoxyimino)acetamido]-3-methoxymethyl-3-cephem-4-carboxylic acid 1-(isopropoxycarbonyloxy)ethyl ester
Cefpodoxime proxetil: 7-[2-(2-aminothiazol-4-yl)-2-(Z)-(methoxyimino)acetamido]-3-methoxymethyl-3-cephem-4-carboxylic acid-1-(isopropoxycarbonyloxy)ethyl ester

EXAMPLE 1

Crystallisation of N-formyl Cefpodoxime Proxetil from Acetone/Water 3 g of amorphous N-formyl cefpodoxime proxetil with a diastereoisomeric ratio B/(A+B) of 0.51 and a HPLC purity of 97% are dissolved in a mixture of 6 ml of DMF and 18 ml of acetone. The solution is heated to 40° and 20 ml of water are added while stirring and after seeding further ca. 40 ml of water are added dropwise while stirring. Crystallisation occurs and the crystalline precipitate is filtrated off and dried. N-Formyl cefpodoxime proxetil in crystalline form is obtained comprising a mixture of diastereoisomers with a diastereoisomeric ratio of B/(A+B)=0.58.

Seed crystals are obtained in preliminary crystallisation tests.

EXAMPLE 2

Crystallisation of N-formyl Cefpodoxime Proxetil from Acetonitrile/Water a) Is carried out as example 1, with the following differences:
15 ml acetonitrile instead of 18 ml acetone
room temperature instead of heating to 40°
adding further 30 ml water instead of 40 ml.
N-Formyl cefpodoxime proxetil in crystalline form is obtained comprising a mixture of diastereoisomers with a diastereoisomeric ratio B/(A+B)=0.56. HPLC purity: 98.7% b) Is carried out as example 2a), with the following differences:
3 ml of DMF and 10 ml of acetonitrile instead of 6 ml of DMF and 15 ml of acetonitrile
12 ml of water instead of 20 ml
adding further 38 ml of water instead of 40 ml.
N-Formyl cefpodoxime proxetil in crystalline form is obtained comprising a mixture of diastereoisomers with a diastereoisomeric ratio B/(A+B)=0.53. HPLC purity. 98.1%

EXAMPLE 3

Crystallisation of N-formyl Cefpodoxime Proxetil from Reaction Solutions a) Preparation of AMCA-Ester
Solution A):

A suspension of 50 g of AMCA in 1000 ml of acetone is mixed with 28.8 g of DBU and the mixture obtained is stirred at room temperature. The solution obtained is cooled to 0°, mixed with 437 g of a 14% toluene solution of 1-iodoethyl-isopropyl carbonate and stirred for ca. 4 hours at ca. 0°. A suspension is obtained and the solid is filtrated off. The filtrate is poured onto water/conc. HCl, and the pH of the mixture obtained is adjusted to 1.0 From the two-phase system obtained, the organic phase is separated off and extracted with water. 1000 ml of ethyl acetate is added to the aqueous phase obtained, and a pH of 8.2 is adjusted with 5N NaOH. The aqueous phase of the two-phase system obtained is separated off and extracted with ethyl acetate. The organic phase obtained is washed with $NaHCO_3$ solution and water and dried over $MgSO_4$. A solution of AMCA-ester in 1100 ml of ethyl acetate (SOLUTION A) is obtained with a content of 5.7% of AMCA-ester in a diastereoisomeric ratio of B/(A+B)= 0.49.

b) Activation of (2-N-formylaminothiazol-4-yl)-2-(Z)-(methoxyimino)-acetic acid

Solution B):

A mixture of 21.4 ml of ethyl acetate, 5.8 ml of DMF, 1.13 ml of phosphorus oxychloride and 2.82 g of (2-N-formylaminothiazol-4-yl)-2-(Z)-(methoxyimino)-acetic acid is stirred for ca. one hour at ca. −10°. The solution obtained is cooled to ca. −25°.

c) Preparation of N-Formyl Cefpodoxime Proxetil

To a solution of 4.29 g of $KHCO_3$ in 41.1 ml of ice-cooled water, 93 ml of SOLUTION A) containing 0.0124 mol of AMCA-ester, and SOLUTION B), cooled to −25°, are added in such a way that the temperature of the mixture remains at ca. 5°. The mixture obtained is stirred for ca. 30 minutes at ca. 5°. The phases of the two-phase system obtained are separated. 20 ml of water are added to the organic phase and the pH is adjusted to 7.1 with $KHCO_3$ while stirring. The phases of the two-phase system obtained are separated. Water is added to the organic phase, and the pH is adjusted to ca. 1.3 with 5 m $H_2SO_4$. The mixture obtained is stirred, the phases of the two-phase system are separated and the organic phase is washed with water and treated with 6.3 ml of DMF. Ethyl acetate is removed from the mixture obtained and the evaporation residue is mixed with 23 ml of acetonitrile. The mixture obtained is heated to 40° and 27 ml of water are added dropwise. After addition of seeds a further 90 ml of water at 40° while stirring. The obtained crystalline precipitate is filtrated off from the reaction mixture and dried. N-Formyl cefpodoxime in crystalline form and in the form of a diastereoisomeric mixture is obtained with a diastereoisomeric ratio of B/(A+B)=0.50 and an HPLC purity of 97.8%.

Seed crystals are obtained in preliminary crystallisation tests.

EXAMPLE 4

Crystallisation of N-formyl Cefpodoxime Proxetil from Reaction Solutions a) AMCA-Ester

SOLUTION A)

A suspension of 50 g of AMCA in 500 ml of dichloromethane is mixed with 28.8 g of DBU and the mixture obtained is stirred at room temperature. The solution obtained is cooled to ca. 0°, mixed with 437 g of a 14% toluene solution of 1-iodoethyl-isopropyl carbonate and the mixture obtained is stirred for ca. 4 hours at ca. 0°. The mixture obtained is mixed with 1000 ml of toluene and the mixture obtained is filtered. The filtrate obtained is worked up according to the method as described in example 3a). A solution of AMCA-ester in toluene is obtained with an AMCA-ester content of 5.8% in the form of a diastereoisomere mixture with a diastereoisomeric ratio of B/(A+B)= 0.49.

b) (2-N-formylaminothiazol-4-yl)-2-(Z)-(methoxyimino)-acetic Acid Chloride in the Form of a hydrochloride A suspension of 60 g of (2-N-formylaminothiazol-4-yl)-2-(Z)-(methoxyimino)-acetic acid in 600 ml of dichloromethane, cooled to ca. −10° is treated with 60 g of $PCl_5$ while stirring, at a temperature below ca. −5°. The suspension obtained is stirred for ca. 90 minutes at ca. −5° to 0°. A precipitate forms in the reaction mixture obtained and is filtrated off, washed and dried. Solid 2-N-formylaminothiazol-4-yl)-2-(Z)-methoxyimino acetic acid chloride in the form of a hydrochloride is obtained.

c) N-Formyl Cefpodoxime Proxetil

To a solution of 2.73 g of $KHCO_3$ in 46.6 ml of ice-cooled water are added 89.2 ml of SOLUTION A) containing 0.0124 mol of AMCA-ester. The mixture obtained is diluted with 8.6 ml of ethyl acetate and 3.45 g of (2-N-formylaminothiazol-4-yl)-methoxyimino)-acetic acid chloride-hydrochloride, produced according to example 4b), are added in such a way that the temperature of the mixture does not exceed ca. 5°. The mixture obtained is stirred for ca. 30 minutes at ca. 5°. The phases of the two-phase system obtained are separated. To the organic phase 23.3 ml of water and 0.5 ml of DMF are added and the pH is adjusted to ca. 7.5 with $KHCO_3$. The phases of the two-phase system obtained are separated, 23.3 ml of water and 0.5 ml of DMF are added to the organic phase, and the pH is adjusted to 1.5 with 5 m $H_2SO_4$. The phases of the two-phase system obtained are separated and the organic phase is washed with water and DMF. 6.3 ml of DMF are added to the organic phase obtained and ethyl acetate is removed by evaporation. The evaporation residue obtained is mixed with 6.3 ml of DMF and 45 ml of acetonitrile. The mixture obtained is heated to ca. 35° and 55 ml of water and a further 179 ml of water are added after seeding dropwise over the course of 40 minutes. The crystalline precipitate from the suspension obtained is filtrated off, washed with water and dried. N-Formyl cefpodoxim proxetil in the form of a diastereoisomere mixture with a diastereoisomeric ratio of B/(A+B)=0.51 in an HPLC purity of 98.0% is obtained.

Seed crystals are obtained in preliminary crystallisation tests.

EXAMPLE 5

Cefpodoxime Proxetil 20 ml of methanol and 0.48 ml of conc. $H_2SO_4$ are mixed and 4.0 g of N-formyl cefpodoxime proxetil obtained according to example 3c) are added to the mixture obtained. A solution is obtained, is stirred at room temperature for ca. 85 minutes, and is added dropwise, whilst stirring to a solution of 2 g of KHCO₃ in 200 ml of water. Cefpodoxime proxetil precipitates, is isolated, washed with water and dried. Cefpodoxime proxetil in the form of a diastereoisomeric mixture with a diastereoisomeric ratio of B/(A+B)= 0.51 and of an HPLC purity of 97.4% is obtained.

What is claimed is:

1. A process for preparing a mixture of diastereoisomers of cefpodoxime proxetil of Formula II

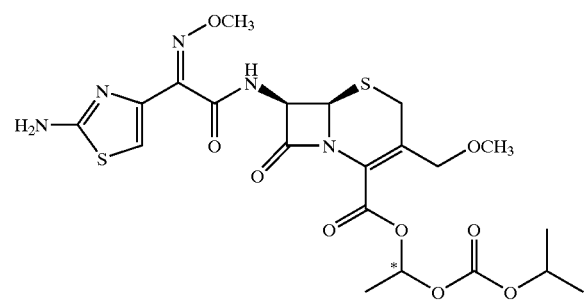

in a diastereoisomeric ratio B/(A+B) of 0.4 to 0.7. wherein B is the more apolar of the two diastereoisomers, wherein the chiral center is marked with a (*), said process comprising (i) acylating a compound of Formula III

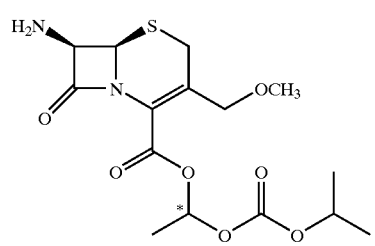

with Z-(2-formamidothiazol-4-yl)-methoxyimino acetic acid, to form a mixture of diastereoisomers of a compound of Formula I

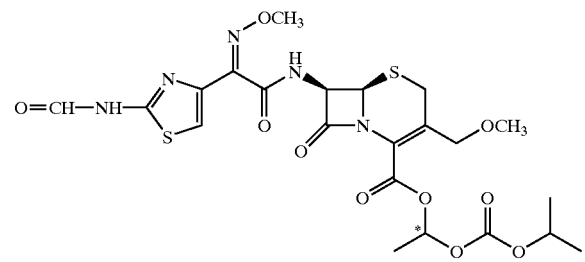

(iii) dissolving the mixture of diastereoisomers of a compound of Formula I in a solvent selected from the group consisting of a nitrile, a ketone, and mixtures thereof, to form a solution, wherein the amount of nitrile is 2–15 ml, based on 1 gm of the compound of Formula I, and the amount of ketone is 3–15 ml, based on 1 gm of the compound of Formula I;

(iv) treating the solution with water to induce precipitation of the compound of Formula I in crystalline form, wherein the amount of water in the case of a nitrile solvent is 5–80 ml, based on 1 gm of the compound of Formula I, and the amount of water in the case of a ketone solvent is 10–40 ml, based on 1 gm of the compound of Formula I;

(v) isolating the compound of Formula I in crystalline form; and (vi) hydrolyzing the compound of Formula I in crystalline form to form a diastereoisomeric mixture in a ratio of B/(A+B) of 0.4 to 0.7 of a compound of Formula II.

2. The process according to claim 1 wherein the diastereoisomeric mixture is in a ratio of B/(A+B) of 0.5 to 0.6.

3. The process according to claim 1 wherein the nitrile is selected from the group consisting of acetonitrile, propionitrile, butyronitrile, and mixtures thereof.

4. The process according to claim 3 wherein the nitrile is acetonitrile.

5. The process according to claim 1 wherein the ketone is selected from the group consisting of acetone, methyl ethyl ketone, and mixtures thereof.

6. The process according to claim 5 wherein the ketone is acetone.

7. A process for preparing a compound of Formula I in crystalline form

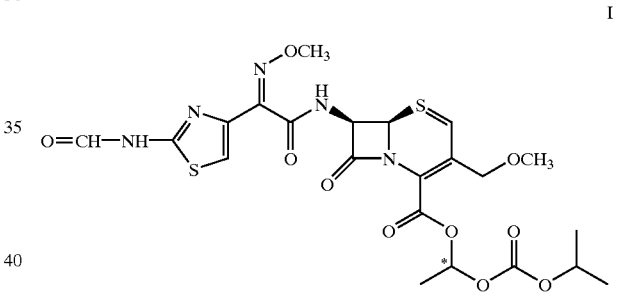

said process comprising:

(a) dissolving a compound of Formula I in a solvent selected from the group consisting of a nitrile, a ketone, and mixtures thereof, to form a solution, wherein the amount of nitrile is 2–15 ml, based on 1 gm of the compound of Formula I, and the amount of ketone is 3–15 ml, based on 1 gm of the compound of Formula I;

(b) treating the solution with water to induce precipitation of the compound of Formula I in crystalline form, wherein the amount of water in the case of a nitrile solvent is 5–80 ml, based on 1 gm of the compound of Formula I, and the amount of water in the case of a ketone solvent is 10–40 ml, based on 1 gm of the compound of Formula I; and (c) isolating the compound of Formula I in crystalline form.

8. A compound having Formula I

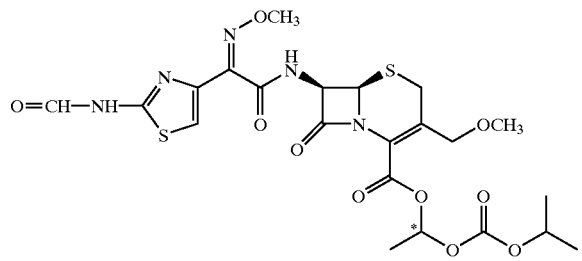

as a diastereoisomeric mixture in crystalline form having a diastereoisomeric ratio B/(A+B) is 0.4 to 0.7, wherein B is the more apolar of the two diastereoisomers, wherein the chiral center is marked with a (*).

9. The compound according to claim 8 wherein the diastereoisomeric ratio B/(A+B) is 0.5 to 0.6.

10. The compound according to claim 8 which is crystalline 7-[2-(2-formylaminothiazol-4-yl)-2-(Z)-(methoxyimino)acetamido]-3-methoxymethyl-3-cephem-4-carboxylic acid-1-(isopropoxycarbonyloxy)ethyl ester.

* * * * *